(12) United States Patent
Brandstadt et al.

(10) Patent No.: US 7,078,519 B2
(45) Date of Patent: Jul. 18, 2006

(54) ENZYME CATALYZED ORGANOSILICON CARBOHYDRATES

(75) Inventors: Kurt Friedrich Brandstadt, Frankenmuth, MI (US); Thomas Howard Lane, Midland, MI (US); Richard A. Gross, Plainview, NY (US)

(73) Assignees: Dow Corning Corporation, Midland, MI (US); Polytechnic University, Brooklyn, NY (US)

( * ) Notice: Subject to any disclaimer, the term of this patent is extended or adjusted under 35 U.S.C. 154(b) by 190 days.

(21) Appl. No.: 10/642,101

(22) Filed: Aug. 15, 2003

(65) Prior Publication Data

US 2004/0077816 A1    Apr. 22, 2004

Related U.S. Application Data

(60) Provisional application No. 60/403,963, filed on Aug. 16, 2002.

(51) Int. Cl.
*C07H 11/00*    (2006.01)
*C08G 2/00*    (2006.01)

(52) U.S. Cl. .................. 536/115; 536/124; 536/120; 536/121; 536/4.1; 536/17.1; 527/300; 556/479; 556/465; 524/492

(58) Field of Classification Search ............... 536/115, 536/124, 120, 121, 4.1, 17.1; 556/479, 465; 514/313; 524/492; 528/15; 546/104; 527/300
See application file for complete search history.

(56) References Cited

U.S. PATENT DOCUMENTS 5,831,080 A * 11/1998 Sejpka et al. ............... 536/124

5,891,977 A    4/1999 Dietz et al.
5,981,743 A * 11/1999 Gross et al. ............. 536/123.1
6,218,560 B1    4/2001 Abele et al.
6,288,129 B1    9/2001 Gruning et al.

FOREIGN PATENT DOCUMENTS

JP    04262794    9/1991
JP    2002119840 A    10/2000

OTHER PUBLICATIONS

Qiu et al., Lipase-catalyzed bioconversion of organosilyl alcohol in microaquous phase, Huanan Ligong Daxue Xuebo, Ziran Kexueban, Jan. 1, 1997, pp. 51-54.

Zong et al., Esterification of organosilyl alcohol catalyzed by lipase in organic phase, Gongye Weishengwu, vol. 28, Issue 4, Jan. 1, 1998, pp. 17-20.

(Continued)

*Primary Examiner*—Shaojia Anna Jiang
*Assistant Examiner*—Devesh Khare
(74) *Attorney, Agent, or Firm*—Dinsmore & Shohl LLP (57) ABSTRACT

Methods for forming structurally defined organosilicon carbohydrates are provided. Additionally, structurally defined organosilicon carbohydrates are provided. The structurally defined organosilicon carbohydrates may be formed by contacting a hydrolase enzyme with an organosilicon reactant and a carbohydrate reactant. The enzyme may catalyze the formation of an ester bond between carboxylic acid, ester, or amide functional groups of the organosilicon or carbohydrate reactant and alcohol functional groups of the carbohydrate or organosilicon reactant. The enzyme may catalyze the formation of an amide bond between carboxylic acid, ester, or amide functional groups of the organosilicon or carbohydrate reactant and amine functional groups of the carbohydrate or organosilicon reactant.

35 Claims, 2 Drawing Sheets

OTHER PUBLICATIONS

Zong et al., Enhancement of lipase-catalyzed esterification in organic solvent by ultrasonic irradiation, Huanan Ligong Daxue Xuebao, Ziran Kxueban, vol. 28, No. 3, Jan. 1, 2000, pp. 101-104.

Qiu et al., Lipase from candida cylindracea catalyzed organosilicon alcohol esterification in organic solvent, Gongye Weishengwu, vol. 27, Issue 3, Jan. 1, 1997, pp. 16-19.

Aouf et al., Preparation and enzymic cleavage of chiral acetoxymethyl- and hydroxymethylsilanes, Phosphorus, Sulfur Silicon Relat. Elem. vol. 88, Issue 1-4, Jan. 1, 1994, pp. 207-215.

Qiu et al., Abstract: Influence of water content on C. cylindracea lipase-catalyzed bioconversion of organosllicon compounds, Guizhou Gongye Daxue Xuebao, vol. 27, Issue 4, Jan. 1, 1998, pp. 91-96.

Qiu et al., Abstract: Interesterification of trimethyisilyl alcohol catalyzed by C cylindraces lipase in organic medium, Guizhou Gongye Daxue Xuebao, Ziran Kexueban, vol. 28, Issue 5, Jan. 1, 1999, pp. 79-83.

Burgess et al., Enantioselective Esterifications of Unsaturated Alcohols Mediated by a Lipase Prepared from Pseudomonas sp., J. Am. Chem. Soc. 1991, 113, pp. 6129-6139.

Sparks et al., Lipase Mediated Resolution of Chiral (E)-Vinylsilanes: An Improved Procedure for the Production of (R)- and (S)-(E)-1-Trialkylsilyl-1-Buten-3-OL Deriviatives, Tetahedron Letters, vol. 32, No. 33, 1991, pp. 4085-4088.

Davoli et al., A Novel Approach to a Precursor of the Carbapenem Antibiotic PS-5 via Aziridine Stereospecific Carbonylation, Heterocycles, vol. 53, No. 11, 2000, pp. 2379-2389.

Gill et al., Lipase-Silicone Biocomposites: Efficient and Versatile Immobilized Biocatalysts, Journal of the American Chemical Society, vol. 121, No. 41, Oct. 20, 1999, pp. 9487-9496.

Luisi, Enzymes Hosted in Reverse Micelles in Hydrocarbon Solution, Angewandte Chemie, International Edition in English, vol. 24, No. 6, Jun. 1985, pp. 439-450.

Hood et al., Polyester Resin Synthesis Techniques For Achieving Lower VOC And Improved Coating Performance, Journal of Coatings Technology, vol. 58, No. 739, Aug. 1986, pp. 49-52.

Kawamoto et al., Enzymatic Preparation of Optically Active Silicon-Containing Amino Acids and Their Application, Applied Biochemistry and Biotechnology, vol. 88, 2000, pp. 17-22.

Kawamoto et al., Efficient optical resolution of 2-(4-chlorophenoxy) propanoic acid with lipase by the use of organosilicon compounds as substrate: the role of silicon atom in enzymatic recognition, Journal of Biotechnology, 18, 1991, pp. 85-92.

Fukui et al., Enzymatic Preparation of Optically Active Silylmethanol Derivatives Having A Stereogenic Silicon Atom by Hydrolase-catalyzed Enantioselective Esterification, Tetrahedron: Asymmetry, vol. 5, No. 1, 1994, pp. 73-82.

Uejima et al., Efficient kinetic resolution of organosilicon compounds by stereoselective esterification with hydrolases in organic solvent, Appl Microbiol Biotechnol, 1993, 38, pp. 482-486.

Gross et al., Polymer Synthesis by In Vitro Enzyme Catalysis, Chem Rev., 2001, 101, pp. 2097-2124.

Tanaka, Chapter 1 Biochemical Approach Biochemical Reactions in Organic Solvents, Kagaku, Zokan 1991, 119, pp. 63-71.

Adelhorst et al., Enzyme Catalysed Preparation of 6-O-Acylglucopyranosides, Synthesis, Feb. 1990, pp. 112-115.

Kobayashi et al., Enzymatic Polymerization, Chem. Rev. 2001, 101, pp. 3793-3818.

Zong et al., Bioconversion of organosilicon compounds by horse liver alcohol dehydrogenase: the role of the silicon atom in enzymatic reactions, Appl Microbiol Biotechnol, 1991, 36, pp. 40-43.

Tsuji et al., Enantioselective dehydrogenation of β-hydroxysilanes by horse liver alcohol dehydrogenase with a novel in-situ NAD+ regeneration system, Appl Microbiol Biotechnol, 1994, 41, pp. 219-224.

Yamanaka et al., Enzymatic preparation of optically active 3-trimethylsilylalanine, Appl Microbiol Biotechnol, 1996, 45, pp. 51-55.

Tsuji et al., Enzymatic preparation of D-ρ -trimethylsilylphenylalanine, Appl Microbiol Biotechnol, 1997, 47, pp. 114-119.

Kawamoto et al., Enzymatic Conversion of Organosilicon Compounds in Organic Solvents, Methods in Biotechnology, vol. 15: Enzymes in nonaqueous solvents: Methods and Protocols, Humana Press, Inc., Totowa NJ, 2001, pp. 339-355.

Braunmuhl et al., Enzymatic Grafting of Amylose from Poly(dimethylsiloxanes), Macromolecules, 1995, 28, pp. 17-24.

Braunmuhl et al., Polydimethylsiloxanes with Amylose Side Chains by Enzymatic Polymerization, Macromol. Symp. 103, 1996, pp. 141-148.

Klibanov, Enzymatic catalysis in anhydrous organic solvents, TIBS 14, Apr. 1989, pp. 141-144.

Tanaka et al., Organosilicon Biochemistry, Annals New York Academy of Sciences, 1990, 613, (Enzyme Eng. 10), pp. 702-706.

Tanaka, Seeking possibilities of enzymes—Biochemical conversion of organosilicon compounds, Nippon Oyo Koso Kyokaishi, 1994, 28, pp. 10-17.

Reetz et al., Efficient Immobilization of Lipases by Entrapment in Hydrophobic Sol-Gel Materials, Biotechnology and Bioengineering, vol. 49, 1996, pp. 527-534.

Ishikawa et al., Enzymatic synthesis of silicon-containing dipeptides with 3-trimethylsilylalanine, Appl Microbiol Biotechnol, 1999, 51, pp. 470-473.

Bjorkling et al., A HIghly Selective Enzyme-catalysed Esterification of Simple Glucosides, J. Chem. Soc., Chem. Commun., 1989 pp. 934-935.

Kumar et al., Synthesis of novel Silicon-based Macromers and Polymers by Enzymatic Catalysis, Polymeric Materials: Science & Engineering 2003, 88, pp. 429-430.

* cited by examiner

ENZYME CATALYZED ORGANOSILICON CARBOHYDRATES

CROSS REFERENCE TO RELATED APPLICATION

This application claims priority to U.S. Provisional Application No. 60/403,963, filed Aug. 16, 2002.

BACKGROUND OF THE INVENTION

The present invention relates to the formation of organosilicon molecules utilizing an enzymatic catalyst, and more specifically to the formation of organosilicon carbohydrates utilizing a hydrolase enzyme and to the organosilicon carbohydrates formed thereby.

Esterification reaction conditions have traditionally inhibited the synthesis of structurally defined organosilicon carbohydrates having ester bonds. Typically, ester materials are synthesized with an acid or base catalyst at high temperatures for long periods. Although these reaction conditions favor the equilibrium of polycondensation, they also promote uncontrolled side reactions, redistribution of monomer sequences, cross linking, and broad molecular weight distributions. In addition, the usual acid and base catalysts are not regioselective and may catalyze esterification for all reactive groups on a polyfunctional monomer. While reasonable reaction rates and conversions may be achieved through acid or base catalysis, these catalysts may also induce the decomposition of potentially useful functional groups, such as epoxy groups, and bonds, such as siloxane bonds.

Typically, traditional methods of synthesizing amide compounds are not selective. For example, the methods may not be regioselective or enantioselective. Therefore, methods of synthesizing amides may not provide the ability to control the material structure.

Thus, the need remains in the relevant art for improved methods of forming structurally defined organosilicon carbohydrates and the novel organosilicon carbohydrate compounds that are made using such methods.

SUMMARY OF THE INVENTION

In accordance with an embodiment of the present invention, an organosilicon carbohydrate is provided. The organosilicon carbohydrate comprises a compound having the formula:

wherein:
each $R^1$ is independently selected from alkyl, haloalkyl, unsaturated alkyl, aryl, hydroxy, alkoxy, hydrogen, —$(OSiR^1{}_2)_x$—$OSiR^1{}_3$, or R''';

at least one of $R^1\nabla R'''$;
x is 0 or greater than 0;
y is equal to or greater than 3; and
R''' is:

wherein:
A is a substituted or unsubstituted hydrocarbon substituent, wherein said hydrocarbon may be substituted such that said hydrocarbon comprises a halogen-, ether-, alkoxy-, phenyl-, or unsaturated-functional hydrocarbon and combinations thereof;
$R^2$ is a carbohydrate; and
m is 0 or greater than 0.

In accordance with another embodiment of the present invention, a method of forming an organosilicon carbohydrate is provided. The method comprises contacting a hydrolase enzyme with an organosilicon reactant and a carbohydrate reactant, wherein:

the organosilicon reactant comprises a organosilicon having the formula wherein:
each R is independently selected from alkyl, haloalkyl, unsaturated alkyl, aryl, hydroxy, alkoxy, hydrogen, —$(OSiR_2)_x$—$OSiR_3$, or R';
at least one of R=R';
x is 0 or greater than 0;
y is equal to or greater than 3; and R' is:

wherein:
A is a substituted or unsubstituted hydrocarbon substituent, wherein said hydrocarbon may be substituted such that said hydrocarbon comprises a halogen-, ether-, alkoxy-, phenyl-, or unsaturated-functional hydrocarbon and combinations thereof;
R" is independently carboxylic acid, ester, alcohol, amide, or amine; and
m is 0 or greater than 0.

Additionally, the carbohydrate reactant comprises a carbohydrate having at least one functional group, wherein: the functional group is selected such that the at least one functional group comprises an alcohol functional group or amine functional group when at least one of the R" comprises carboxylic acid, ester, or amide; and the at least one functional group comprises a carboxylic acid functional group, ester functional group, or amide functional group when at least one of the R" comprise alcohol or amine. The enzyme catalyzes the formation of an organosilicon carbohydrate, and the organosilicon carbohydrate is formed such that: the enzyme catalyzes the formation of an ester bond between carboxylic acid, ester, or amide functional groups of the organosilicon reactant or the carbohydrate reactant and alcohol functional groups of the carbohydrate reactant or the organosilicon reactant to form said organosilicon carbohydrate; or the enzyme catalyzes the formation of an amide bond between carboxylic acid, ester, or amide functional groups of the organosilicon reactant or the carbohydrate reactant and amine functional groups of the carbohydrate reactant or the organosilicon reactant to form the organosilicon carbohydrate.

DETAILED DESCRIPTION OF THE PREFERRED EMBODIMENTS

The present invention utilizes hydrolase enzymes to form structurally defined organosilicon carbohydrates.

Unless otherwise indicated, all numbers expressing quantities of ingredients, properties such as molecular weight, reaction conditions, and so forth as used in the specification and claims are to be understood as being modified in all instances by the term "about." Accordingly, unless otherwise indicated, the numerical properties set forth in the following specification and claims are approximations that may vary depending on the desired properties sought to be obtained in embodiments of the present invention. Notwithstanding that the numerical ranges and parameters setting forth the broad scope of the invention are approximations, the numerical values set forth in the specific examples are reported as precisely as possible. Any numerical values, however, inherently contain certain errors necessarily resulting from error found in their respective measurements.

The present invention relates to the reaction of an organosilicon reactant and a carbohydrate reactant in the presence of a hydrolase enzyme to form organosilicon carbohydrates. The reaction involves the formation of an ester bond between at least one carboxylic acid, ester, or amide functional group and at least one alcohol functional group. Alternatively, the reaction involves the formation of an amide bond between at least one carboxylic acid or ester functional group and at least one amine functional group or between an amide functional group and an amine functional group as shown in the reaction sequences below:

In the above reactions, X and Y represent a portion of an organosilicon or carbohydrate compound other than the carboxylic acid, ester, alcohol, amine, or amide functional groups. It will be understood that the ester or amide functional groups are not limited to the methylated ester or amide as shown in the above reactions. Rather, the ester or amide functional group may have any desired group substituted for the methyl group shown.

The organosilicon reactant is an organosilicon species. The organosilicon reactant may be a silane or may have at least one siloxane bond. The organosilicon reactant generally has at least one carboxylic acid, ester, amine, alcohol, or amide functional group, and the organosilicon reactant may be monofunctional or polyfunctional. The carboxylic acid, ester, amine, alcohol, or amide functional groups may be pendant, terminal, or be in any other suitable location. However, the carboxylic acid, ester, amine, alcohol, or amide functional groups may not be directly bonded to the silicon. The organosilicon reactant may be linear, branched, resinous, or cyclic. Suitable linear, branched, or resinous organosilicon reactants having at least one siloxane bond generally correspond to Formula (I), suitable cyclic organosilicon reactants having at least three siloxane bonds generally correspond to Formula (II), and suitable silane reactants generally correspond to Formula (III), all as shown below:

Formula (I)

Formula (II)

Formula (III)

wherein:
each R is independently selected from alkyl, haloalkyl, unsaturated alkyl, aryl, hydroxy, alkoxy, hydrogen, —(OSiR$_2$)$_x$—OSiR$_3$, or R';
at least one of R=R';
x is 0 or greater than 0;
y is equal to or greater than 3; and
R' is:

wherein:
A is a substituted or unsubstituted hydrocarbon substituent, wherein said hydrocarbon may be substituted such that said hydrocarbon comprises a halogen-, ether-, alkoxy-, phenyl-, or unsaturated-functional hydrocarbon and combinations thereof;
R" is independently carboxylic acid, ester, alcohol, amide, or amine; and
m is 0 or greater than 0.

In accordance with an embodiment of the present invention, x may be between 0 to about 250. The organosilicon reactant may be selected such that y is between about 3 to about 6. The organosilicon reactant may be selected such that A comprises a C$_3$ to C$_{20}$ hydrocarbon, and m is between 0 and about 250.

It will be understood by those skilled in the art that the portion of the organosilicon structure shown within the brackets of Formulas (I) and (II) do not have to be identical repeating units. Rather, the R groups may be independently chosen for each of the repeating units. It will be understood that alkyl, haloalkyl, unsaturated alkyl, alkoxy, and hydrocarbon may be substituents having one carbon or more than one carbon. It will be further understood that, when A is a substituted hydrocatbon, the substitutions may be in the middle of the carbon chain or pendant on the carbon chain. However, the substitution will not generally be terminal on the end of the carbon chain next to R". The organosilicon reactants of Formulas (I), (II), and (III) are acceptable substrates for the hydrolase enzyme to selectively catalyze the esterification or amidation reaction at the reactive sites of the organosilicon reactant. The reactive sites of the organosilicon reactant comprise the carboxylic acid, ester, amide, alcohol, or amine functional groups. Thus, structurally defined organosilicon carbohydrates may be formed using the organosilicon reactants of Formulas (I), (II), and (III).

A carbohydrate is used as a reactant in the formation of organosilicon carbohydrates. For purposes of defining and describing the present invention "carbohydrate" shall be understood as referring to a sugar, starch, or cellulose and combinations thereof. The carbohydrate has at least one alcohol, amine, carboxylic acid, ester, or amide functional group. Additionally, the carbohydrate may be silicon functional.

Generally, the at least one functional group of the carbohydrate comprises an alcohol functional group or amine functional group when at least one of R" of Formulas (I-III) comprises carboxylic acid, amide, or ester. The at least one functional group of the carbohydrate comprises a carboxylic acid functional group, ester functional group, or amide functional group when at least one of R" of Formulas (I-III) comprise alcohol or amine. It will be understood that the carbohydrate may have more than one functional group, and it will be further understood that the functional groups may be the same functional group or different functional groups.

In accordance with an embodiment of the present invention, the carbohydrate reactant may be a sugar. In accordance with an embodiment of the present invention, the sugar may be a polysaccharide having more than 20 sugar units. In accordance with a further embodiment of the present invention, the sugar may be an oligosaccharide having less than 20 sugar units. In accordance with a further embodiment of the present invention, the sugar may be a monosaccharide or a disaccharide.

In accordance with an embodiment of the present invention, the carbohydrate reactant may be a cellulose. The cellulose may be chosen such that the cellulosic material is dispersible in a liquid medium. By "dispersible in a liquid medium" it is meant cellulosic materials having nano- or micro-sized fibers that may be dispersed in an appropriate liquid medium. The cellulose may alternatively be chosen such that the cellulosic material is non-dispersible in a liquid medium.

In accordance with an embodiment of the present invention, the carbohydrate may be modified such that it is in a liquid form. For example, glucose may be modified to form ethyl glucoside, which is an oil, as described in Bjorkling, F. et al., *J. of Am. Chem. Soc. Communication* 1989, 934–935 and Adelhorst, K. et al., *Synthesis* 1990, 112–115. Such modifications of the carbohydrate allow a liquid to liquid reaction between the carbohydrate and the organosilicon reactant, and the reaction may occur in bulk. In accordance with another embodiment of the present invention, the carbohydrate or organosilicon may be a solid and the reaction may be between a liquid and a solid. When the carbohydrate or organosilicon is in the form of a solid, the reactions of the present invention may occur on the surface of the solid. Thus, the surface of the solids may be modified.

The organosilicon and the carbohydrate are contacted with a hydrolase enzyme in order to catalyze the formation of the amide or ester bond. It will be understood that the organosilicon and carbohydrate may be contacted with the hydrolase enzyme sequentially. The hydrolase enzyme is generally an esterase, lipase, or protease and combinations thereof, and the hydrolase enzyme is more generally lipase or protease. The hydrolase enzyme may be derived from a bacterial, fungal, or mammalian source, or the hydrolase enzyme may be derived from any other suitable source. For example, the hydrolase enzyme may be Novozyme 435® (N435) lipase available from Novozyme (Bagsvaerd, Denmark), *Candida cylindricia* lipase type VII (CCL) available from Sigma (St. Louis, Mo.), porcine pancreatic lipase (PPL) available from Sigma (St. Louis, Mo.), and protease enzymes such as subtilisin and papain available from Sigma (St. Louis, Mo.). The enzyme is generally present as a heterogeneous suspension, and the enzyme may be lyophilized or immobilized.

The hydrolase enzyme catalyzes the formation of an ester bond between a carboxylic acid, ester, or an amide functional group and an alcohol functional group in a one-step reaction. Alternatively, the hydrolase enzyme catalyzes the formation of an amide bond between a carboxylic acid or an ester functional group and an amine functional group in a one-step reaction. Additionally, the hydrolase enzyme catalyzes the formation of an amide bond between an amine functional group and an amide functional group. Thus, the enzyme catalyzes the formation of an ester bond between carboxylic acid, ester, or amide functional groups of the organosilicon reactant or the carbohydrate reactant and alcohol functional groups of the carbohydrate reactant or the organosilicon reactant to form the organosilicon carbohydrate. Alternatively, the enzyme catalyzes the formation of an amide bond between the carboxylic acid, ester, or amide functional groups of the organosilicon reactant or the carbohydrate reactant and amine functional groups of the carbohydrate reactant or the organosilicon reactant to form the organosilicon carbohydrate. It will be noted by the skilled practitioner that no protection or deprotection steps are required in the formation of the novel compounds of present invention, and the organosilicon reactants are suitable substrates for the enzyme. Thus, the organosilicon carbohydrates may have formulas corresponding to:

Formula (IV)

Formula (V)

Formula (VI)

wherein:

each $R^1$ is independently selected from alkyl, haloalkyl, unsaturated alkyl, aryl, hydroxy, alkoxy, hydrogen, —$(OSiR^1_2)_x$—$OSiR^1_3$, or $R'''$;

at least one of $R^1=R'''$;

x is 0 or greater than 0;

y is equal to or greater than 3; and $R'''$ is:

wherein:

A is a substituted or unsubstituted hydrocarbon substituent, wherein said hydrocarbon may be substituted such that said hydrocarbon comprises a halogen-, ether-, alkoxy-, phenyl-, or unsaturated-functional hydrocarbon and combinations thereof;

$R^2$ is a carbohydrate; and m is 0 or greater than 0.

The formation of the ester or amide bond is regioselective. Generally, the regioselectivity of the enzyme ensures that the resulting organosilicon carbohydrate product is structurally defined and has a defined molecular weight. For example, when N435 lipase is used as the hydrolase enzyme, the esterification reaction is selective to the primary hydroxyl group of ethyl glucoside carbohydrate and the ester bond is formed at the primary hydroxyl group. Thus, a structurally defined organosilicon carbohydrate having an ester bond may be formed. The formation of the ester or amide bond may also be enantioselective.

It will be apparent to those having skill in the art that more than one functional group may be present on a organosilicon reactant and/or on a carbohydrate reactant. Therefore, organosilicon carbohydrate monomers, macromers, and polymers may be formed using the enzymatic method of the present invention. The polymers formed using the enzymatic method may be of any molecular weight and configuration. The polymers may be of the terpolymer type or any other suitable type of polymer. The carbohydrate reactant may be utilized to crosslink the organosilicon carbohydrates.

When an interfacial enzyme is used, the organosilicon reactants appear to enhance the rate of esterification or amidation catalyzed by the enzyme in comparison to the rate of esterification or amidation catalyzed by the enzyme when organic materials are used in place of organosilicon materials. Lipase is an example of an interfacial enzyme. Thus, the use of organosilicon reactants may be advantageous in forming organosilicon carbohydrate materials containing ester and/or amide bonds.

The reactions are generally carried out under mild reaction conditions. The temperature of the reactions is generally between about 20° C. and 100° C., and the reaction is more generally carried out at a temperature of between about 40° C. to about 70° C. No acid or base catalysts are required. The reactions may be performed under solventless (neat) conditions, or the reactions may be performed utilizing a solvent. Suitable solvents include, but are not limited to, hexane, toluene, xylene, and other hydrophobic alkyl or aromatic organic solvents.

The ability to synthesize organosilicon carbohydrates under mild reaction conditions is advantageous because the mild reaction conditions do not cleave the siloxane bonds of the siloxane reactants. Therefore, novel organosilicon carbohydrates may be synthesized. Additionally, the various functional groups of the organosilicon and carbohydrate reactants may be chosen to introduce a desired functionality into the resulting organosilicon carbohydrates. For example, a hydrophobic organosilicon and a hydrophilic carbohydrate may be chosen such that the resulting organosilicon carbohydrate is an amphiphilic molecule having desired surfactant properties. Phenol functional groups may be chosen and then selectively coupled after the formation of the organosilicon carbohydrate to synthesize electrically conductive organosilicon carbohydrates.

The functional groups of the organosilicon carbohydrates may be chosen such that the organosilicon carbohydrate may act in a delivery system, such as a system for delivering proteins or vitamins. Alternatively, the functional groups may be chosen to allow the resulting organosilicon carbohydrate to be used in separation or extraction schemes. Additionally, the carbohydrate may be chosen for its orientation or chiral properties, and the resulting organosilicon carbohydrate may be used for photonic applications. The organosilicon carbohydrates may be formed such that they have the ability to self assemble, and this ability would allow them to be used to form new materials. The organosilicon carbohydrates may also be used to form gels, fibers, films, coatings, and other materials having a desired functionality, such as, for example, adhesiveness or the ability to conduct electricity.

In order that the invention may be more readily understood, reference is made to the following examples, which are intended to be illustrative of the invention, but are not intended to be limiting in scope.

EXAMPLE 1

Lipase (N435) from Novozyme was used to selectively react 1,3-bis(3-carboxypropyl)tetramethyldisiloxane (i.e., diacid disiloxane) with the primary hydroxyl group of ethyl glucoside as shown below wherein x=0 and n=3:

The reaction was run neat at 70° C. for 36 hours. The reaction was formulated with an organosilicon:carbohydrate mole ratio equal to 1:2. The enzyme:monomer weight ratio was 1:10.

The reaction was conducted with constant stirring (i.e., magnetic stir bar) in a two-neck round-bottom flask under vacuum in a heated oil bath. Ethyl glucoside was added to the organosilicon reactant at 70° C. After homogenization, dried N435 was added to the reaction mixture and heated for 36 hours under vacuum. After the reaction, the mixture was filtered to remove the enzyme and the product was purified by silica gel column chromatography with a chloroform:hexane eluent (9:2).

The reactions were monitored by thin layer chromatography. After 36 hours, the reactions were filtered and the products were purified by silica gel column chromatography. The diacid disiloxane product (i.e., a tan fluid) was characterized by $^{13}C$ distortionless enhancement by polarization transfer nuclear magnetic resonance spectroscopy ($^{13}C$ DEPT NMR), electrospray ionization mass spectrometry (ESI MS), Fourier transform infrared spectroscopy (FTIR), gel permeation chromatography refractive index (GPC-RI), thermogravimetric analysis (TGA), and differential scanning calorimetry (DSC). Based on the material characterization, lipase was observed to catalyze a regioselective esterification with ethyl glucoside during the formation of mono- (Rf=0.6, $CHCl_3$:$CH_3OH$ 9:2, isolated yield 19%) and di-ester (Rf=0.4, $CHCl_3$:$CH_3OH$ 9:2, isolated yield 48%)

products. Specifically, N435 catalyzed the formation of an ester bond between the primary hydroxyl group of ethyl glucoside and the diacid disiloxane.

Figure 1:
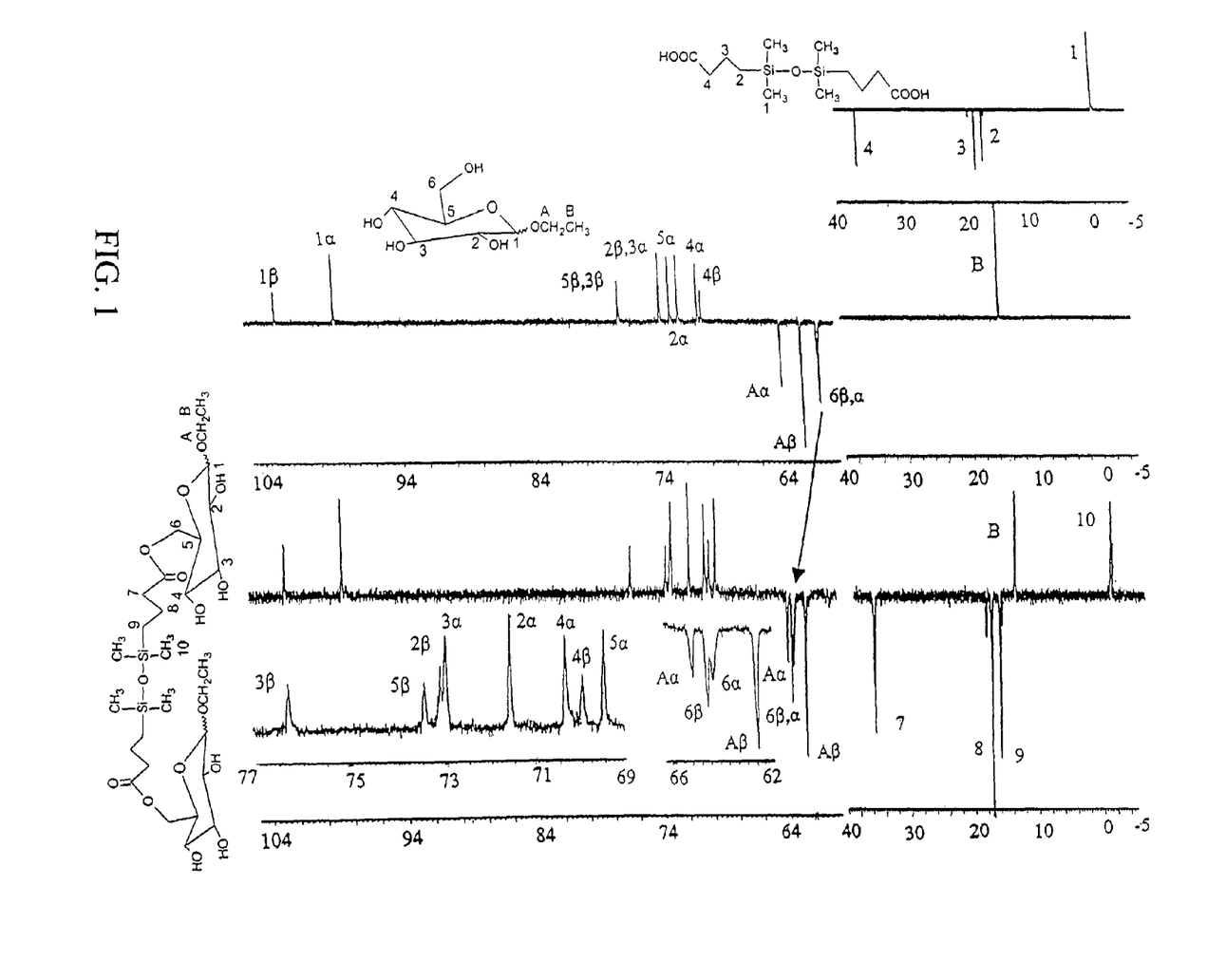
FIG. 1 are $^{13}$C DEPT NMR spectra of the products in Example 1.
Figure 2:
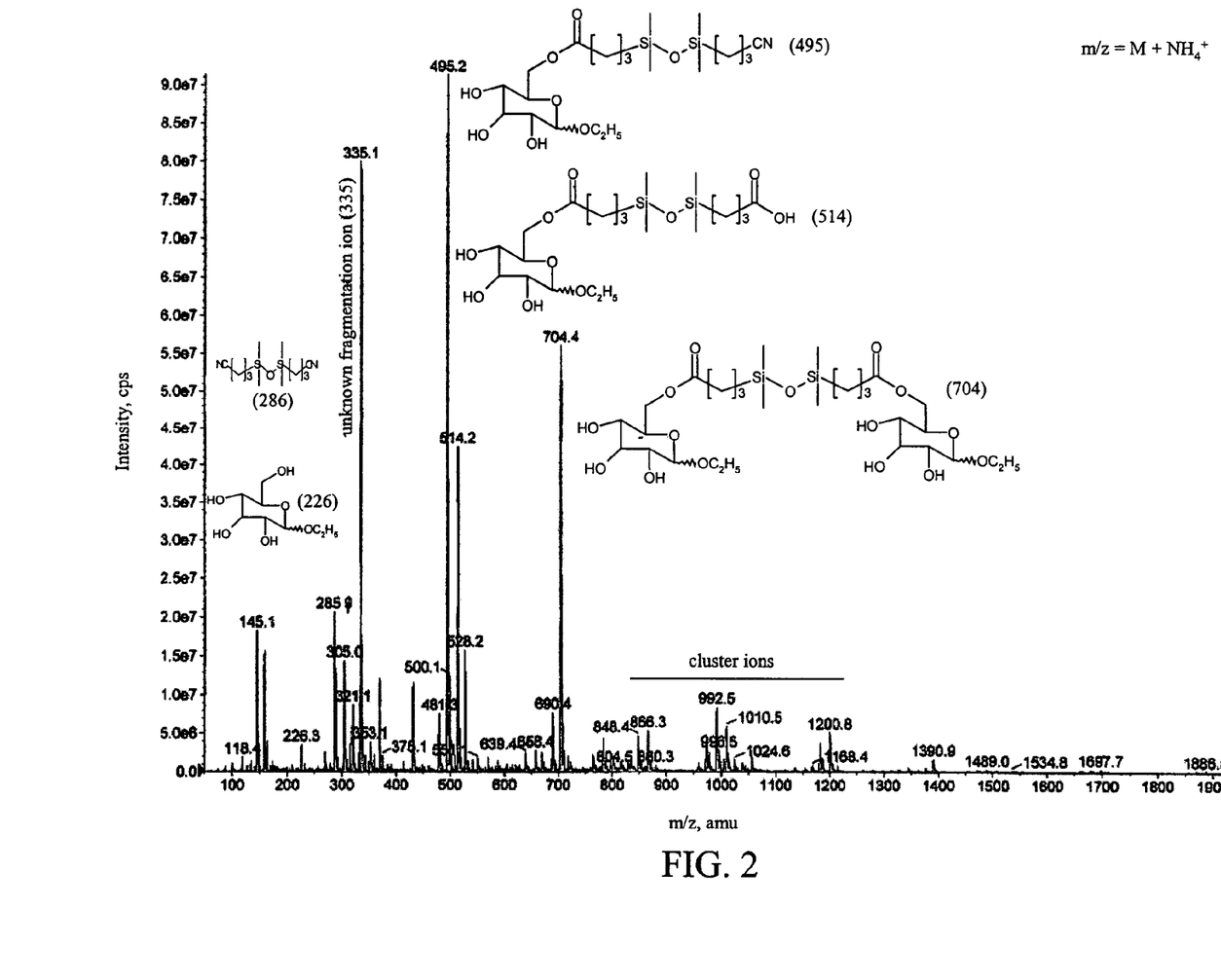
FIG. 2 is an ESI MS analysis of the products in Example 1.

The regioselectivity was confirmed by the DEPT experiment as shown in FIG. 1. The diacid disiloxane spectrum is shown on top. The ethyl glucoside spectrum is shown in the middle, and the ethyl glucoside-functional organosilicon is shown on the bottom. The DEPT experiment was run in DMSO-d6. In the DEPT spectrum of ethylglucoside, the 6α,β carbon (62.1 ppm) shifted 2.1 ppm down field after reaction with the diacid disiloxane. Experimentally, this observation supports the regioselective esterification at the C-6 position. See, Bisht K. S. et. al., *J. Am. Chem. Soc.,* 1998, 120, 1363–1367. Since the C-5 position shifted 3.3 ppm up field and all other peak positions remained unchanged, the regioselective reaction at the C-6 position was confirmed. In the mono-substituted species, the observed C-6 and C-5 peak shifts were the same as the di-substituted species. Similar types of NMR shifts have been reported for carbohydrates bearing hydrophobic chains at the C-6 position of sugars. Furthermore, the ESI MS analysis as shown in FIG. 2 of the product supports the selective formation of an ester bond between one hydroxyl group of the ethyl glucoside molecules and the diacid disiloxane.

The product was analyzed using thermal analysis, and the product was observed to experience a critical mass loss at 184° C. instead of the 164° C. of the diacid disiloxane reactant. Weight loss was observed to occur at two temperatures (281° C., 395° C.) in the product vs. one temperature (226° C.) in the starting material. The Tg was measured to be −28° C. In comparison to the diacid disiloxane (Tg=−76° C.), more energy was required to achieve molecular motion. No crystalline phases were observed in the product. A cold crystallization (Tcc=−15° C., 50.4 J/g) and two crystalline phases (Tm=30° C., 45 J/g; 46° C., 8.6 J/g) were detected in the diacid disiloxane reactant.

EXAMPLE 2

Lipase (N435) from Novozyme was used to selectively react diacid-endblocked polydimethylsiloxane (i.e., diacid PDMS) with the primary hydroxyl group of ethyl glucoside as shown below wherein x=17 and n=10:

The reaction was run neat at 70° C. for 36 hours. The reaction was formulated with an organosilicon:carbohydrate mole ratio equal to 1:2. The enzyme:monomer weight ratios was 1:10.

The reaction was conducted with constant stirring (i.e., magnetic stir bar) in a two-neck round-bottom flask under vacuum. Ethyl glucoside was added to the organosilicon reactant at 70° C. After homogenization, dried N435 was added to the reaction mixture and heated for 36 hours under vacuum. After the reaction, the mixture was filtered to remove the enzyme and the product was purified by silica gel column chromatography with a chloroform:hexane eluent (9:2).

Subsequently, the reaction product was analyzed by $^{13}$C DEPT NMR. Similar to Example 1, the change in chemical shifts observed in the $^{13}$C DEPT NMR analysis further support the regioselective esterification at the C-6 position.

It will be obvious to those skilled in the art that various changes may be made without departing from the scope of the invention, which is not to be considered limited to what is described in the specification.

What is claimed is:

1. An organosilicon carbohydrate comprising a compound having the formula:

wherein:
each $R^1$ is independently selected from alkyl, haloalkyl, unsaturated alkyl, aryl, hydroxy, alkoxy, hydrogen, $—(OSiR^1_2)_x—OSiR^1_3$, or $R'''$;
at least one of $R^1=R'''$;
x is 0 or greater than 0;
y is equal to or greater than 3; and
$R'''$ is:

wherein:
A is a substituted or unsubstituted hydrocarbon substituent, wherein said hydrocarbon may be substituted such that said hydrocarbon comprises a halogen-, ether-, alkoxy-, phenyl-, or unsaturated-functional hydrocarbon and combinations thereof;
$R^2$ is a carbohydrate; and
m is 0 or greater than 0.

2. The organosilicon carbohydrate as claimed in claim 1 wherein x is between 0 and about 250.

3. The organosilicon carbohydrate as claimed in claim 1 wherein A comprises a $C_3$ to $C_{20}$ hydrocarbon substituent.

4. The organosilicon carbohydrate as claimed in claim 1 wherein y is between about 3 to about 6.

5. The organosilicon carbohydrate as claimed in claim 1 wherein m is between 0 and about 250.

6. The organosilicon carbohydrate as claimed in claim 1 wherein $R^2$ comprises a sugar.

7. The organosilicon carbohydrate as claimed in claim 6 wherein $R^2$ is selected from a monosaccharide, a disaccharide, an oligosaccharide, and a polysaccharide.

8. The organosilicon carbohydrate as claimed in claim 6 wherein $R^2$ comprises a monosaccharide.

9. The organosilicon carbohydrate as claimed in claim 6 wherein $R^2$ comprises a disaccharide.

10. The organosilicon carbohydrate as claimed in claim 6 wherein $R^2$ comprises a oligosaccharide.

11. The organosilicon carbohydrate as claimed in claim 6 wherein $R^2$ comprises a polysaccharide.

12. The organosilicon carbohydrate as claimed in claim 1 wherein $R^2$ comprises a starch.

13. The organosilicon carbohydrate as claimed in claim 1 wherein $R^2$ comprises a cellulose.

14. The organosilicon carbohydrate as claimed in claim 13 wherein said cellulose comprises a dispersible cellulosic material.

15. The organosilicon carbohydrate as claimed in claim 13 wherein said cellulose comprises a non-dispersible cellulosic material.

16. The organosilicon carbohydrate as claimed in claim 1 wherein said compound comprises:

17. The organosilicon carbohydrate as claimed in claim 1 wherein said compound comprises:

18. The organosilicon carbohydrate as claimed in claim 1 wherein said compound comprises:

19. The organosilicon carbohydrate as claimed in claim 1 wherein said compound comprises:

20. A method of forming an organosilicon carbohydrate, comprising contacting a hydrolase enzyme with an organosilicon reactant and a carbohydrate reactant, wherein:

said organosilicon reactant comprises a organosilicon having the formula wherein:
each R is independently selected from alkyl, haloalkyl, unsaturated alkyl, aryl, hydroxy, alkoxy, hydrogen, —(OSiR$_2$)$_x$—OSiR$_3$, or R';
at least one of R=R';
x is 0 or greater than 0;
y is equal to or greater than 3; and
R' is:

wherein:
A is a substituted or unsubstituted hydrocarbon substituent, wherein said hydrocarbon comprises a halogen-, ether-, alkoxy-, phenyl-, or unsaturated-functional hydrocarbon and combinations thereof;
R" is independently carboxylic acid, ester, alcohol, amide, or amine; and
m is 0 or greater than 0;
said carbohydrate reactant comprises a carbohydrate having at least one functional group, wherein said functional group is selected such that:
said at least one functional group comprises an alcohol functional group or amine functional group when at least one of said R" comprises carboxylic acid, ester, or amide; and
said at least one functional group comprises a carboxylic acid functional group, ester functional group, or amide functional group when at least one of said R" comprise alcohol or amine;

said enzyme catalyzes the formation of an organosilicon carbohydrate, wherein said organosilicon carbohydrate is formed such that:
said enzyme catalyzes the formation of an ester bond between carboxylic acid, ester, or amide functional groups of said organosilicon reactant or said carbohydrate reactant and alcohol functional groups of said carbohydrate reactant or said organosilicon reactant to form said organosilicon carbohydrate; or
said enzyme catalyzes the formation of an amide bond between carboxylic acid, ester, or amide functional groups of said organosilicon reactant or said carbohydrate reactant and amine functional groups of said carbohydrate reactant or said organosilicon reactant to form said organosilicon carbohydrate.

21. The method as claimed in claim 20 wherein said hydrolase enzyme comprises an esterase, lipase, protease and combinations thereof.

22. The method as claimed in claim 21 wherein said hydrolase enzyme comprises a lipase.

23. The method as claimed in claim 22 wherein said lipase comprises Candida antarctica lipase B.

24. The method as claimed in claim 20 wherein said carbohydrate reactant comprises a solid, and wherein said organosilicon reactant comprises a liquid.

25. The method as claimed in claim 20 wherein said organosilicon reactant comprises a solid, and wherein said carbohydrate reactant comprises a liquid.

26. The method as claimed in claim 20 wherein said organosilicon reactant comprises a liquid, and wherein said carbohydrate reactant comprises a liquid.

27. The method as claimed in claim 20 wherein said organosilicon reactant is selected such that more than one R=R'.

28. The method as claimed in claim 20 wherein said carbohydrate reactant is selected such that said reactant has a plurality of said functional groups.

29. The method as claimed in claim 28 wherein said plurality of functional groups comprise the same functional group.

30. The method as claimed in claim 28 wherein said plurality of functional groups comprise different functional groups.

31. The method as claimed in claim 20 wherein said organosilicon reactant is selected such that more than one R=R', and wherein said carbohydrate reactant is selected such that said reactant has a plurality of said functional groups.

32. The method as claimed in claim 20 wherein said reaction is conducted at a temperature of between about 20° C. to about 100° C.

33. The method as claimed in claim 20 wherein said reaction is conducted at a temperature of between about 40° C. and about 70° C.

34. The method as claimed in claim 20 wherein said reaction is conducted under solventless conditions.

35. The method as claimed in claim 20 wherein said reaction is conducted in a hydrophobic solvent.

* * * * *